United States Patent [19]

Ando et al.

[11] Patent Number: 5,576,299
[45] Date of Patent: Nov. 19, 1996

[54] FORMULATED MEDICINE FOR TREATMENT AND PREVENTION OF OPPORTUNISTIC INFECTIOUS DISEASES COMPLICATED BY INFECTION WITH LENTIVIRUS

[75] Inventors: Kunio Ando, Kanagawa; Junichi Kishimoto, Tokyo, both of Japan

[73] Assignee: Immuno Japan, Inc., Japan

[21] Appl. No.: 25,395

[22] Filed: Mar. 2, 1993

[30] Foreign Application Priority Data

Mar. 2, 1992 [JP] Japan ................................. 4-093933

[51] Int. Cl.$^6$ ................................................. A61K 38/40
[52] U.S. Cl. ........................... 514/21; 530/394; 530/395; 530/400
[58] Field of Search ........................... 530/380, 394, 530/395, 400; 514/21

[56] References Cited

U.S. PATENT DOCUMENTS

| | | | |
|---|---|---|---|
| 4,977,137 | 12/1990 | Nichols et al. | 514/21 |
| 5,093,115 | 3/1992 | Stevenson et al. | 424/85.5 |
| 5,158,979 | 10/1992 | Clarkson, Jr. et al. | 514/575 |
| 5,198,419 | 3/1993 | Ando et al. | 514/8 |

FOREIGN PATENT DOCUMENTS

| | | |
|---|---|---|
| 0205387 | 12/1986 | European Pat. Off. . |
| 0431933 | 6/1991 | European Pat. Off. . |
| 2233619 | 9/1990 | Japan . |

OTHER PUBLICATIONS

Weinberg Physiological Reviews, vol. 64, No. 1 Jan. 1984, pp. 65–102.
Kurth, Intervivology, vol. 31(6), pp. 301–314, 1990.
Tyms et al., J. Antimicrob. Chemother., vol. 23 Suppl A, pp. 89–105, 1989.
Prufer–Kramer et al., Fortschr. Med., vol. 109(7) pp. 169–172, 1991.
Weijmer et al. Lancet (1990), vol. 336, pp. 464–466.

*Primary Examiner*—Chhaya D. Sayala
*Attorney, Agent, or Firm*—Beveridge, DeGrandi, Weilacher & Young, L.L.P.

[57] ABSTRACT

The protein lactoferrin can be used both for treating and/or preventing of portunistic infections frequently complicating Immunodeficiency Virus positive animals including human beings. The protein greatly improves the quality of life in such immunodeficiency virus infected animals. The dosage of the protein is usually 0.1–100 mg/kg daily, and preferably 0.5–50 mg/kg.

8 Claims, No Drawings

FORMULATED MEDICINE FOR TREATMENT AND PREVENTION OF OPPORTUNISTIC INFECTIOUS DISEASES COMPLICATED BY INFECTION WITH LENTIVIRUS

BACKGROUND AND INTRODUCTION

The present invention concerns formulated medicine for treatment and/or prevention of opportunistic infectious diseases complicated by infection with Lentivirus.

AIDS or Acquired Immunodeficiency Syndrome, one of the biggest problems in modern medicine, is an infectious disease caused by a RNA virus called Lentivirus. Viral RNA of Lentivirus, which is a Retrovirus, is transcribed into DNA by the activity of reverse-transcriptase after infection of the host cell, where it acts like a gene of the host cell. Consequently, genetic modification occurs after integration of the viral gene into the host (similar to oncogenesis), and becomes incurable. How to treat and cure the disease remains as one of the biggest problems in modern medicine. This fact causes public fear about AIDS.

HIV-1 and HIV-2, or human Lentivirus, is characterized by destroying lymphocytes having the CD4 receptor and damaging the immune system. Some viruses other than HIV-1 and HIV-2 are classified as Lentivirus: SIV causing immunodeficiency syndrome in monkeys, FIV causing feline immunodeficiency syndrome, goat arthritis virus and encephalitis virus, horse infectious viral anemia, and bovine Immunodeficiency Virus. The diseases caused by these viruses have a common characteristic in these animal species in that the animals become immunodeficient, resulting in frequent complications due to opportunistic infectious diseases. Especially in human AIDS, it is important to treat and prevent opportunistic infectious diseases to improve patients' quality of life and for prolongation of the life span of asymptomatic HIV carriers, and patients with AIDS related syndrome and genuine AIDS. The treatment and prevention of opportunistic infections are as important as the suppression of the viral proliferation using anti-viral drugs.

Opportunistic infectious disease is caused by microbes and viruses having weak pathology which scarcely invade a healthy animal with an intact immune system. Onset of AIDS is triggered by immunodeficiency caused by decrease of CD4 lymphocytes; these compromised conditions are followed by infections by various opportunistic pathogens (which are normally removed by the immune system in healthy animals). Highly characteristic opportunistic infections occur in AIDS patients as follows: pneumonia caused by respiratory infection by protozoan *Pneumocystis carinii*; systemic infection by Cytomegalovirus or Herpes simplex virus; and mycotic infection by Candida or Aspergillus.

In spite of the remarkable progress of antibiotics and synthetic chemotherapies (hereinafter "chemotherapy" for both), opportunistic infectious diseases are regarded as very intractable in compromised hosts (such as those having AIDS). It is known that elimination of pathogens by the host-defense system plays a decisive role during recovery from infectious disease, along with inhibition of proliferation or eradication of pathogens by chemotherapies. Since in most cases opportunistic infectious disease onsets only in a host whose host-defense system faces collapse of integration, and many pathogens begin to propagate simultaneously, it is improbable that a single chemotherapeutic drug can improve the condition. Accordingly, it is clear that opportunistic infectious disease will never be cured completely unless there is a means to restore the host-defense system simultaneously with inhibiting proliferation of pathogens with combined chemotherapies. Some current methods to improve host-defense ability of compromised hosts are known but there is none that improves host-defense ability without any side effect.

SUMMARY OF THE INVENTION

One object of the present invention is to provide formulated medicine for treatment and/or prevention of opportunistic infectious diseases under the immunodeficient conditions caused by Lentiviral infection. Formulated medicine provided by the present invention is characterized by comprising raw but not denatured proteins belonging to the transferrin/lactoferrin family. Although such proteins are widely distributed in animals, the transferrin obtained from mammalian blood, lactoferrin obtained from mammalian milk, and ovo-transferrin obtained from avian albumen are the resources that exist abundantly. These proteins can be economically isolated in a relatively purified state.

DETAILED DESCRIPTION OF THE INVENTION

The protein class of the transferrin/lactoferrin family are large molecules having molecular weights of more than 70,000 Daltons and they can chelate two $Fe^{3+}$ ions. Close conformational similarity in the proteins obtained from different animal species leads to the assumption that they have the same origin and differentiate in each other in the long process of evolution. The protein class of transferrin/lactoferrin isolated from these natural sources contains an iron content reflecting the condition of its source; for example, the degree of saturation of iron ion isolated from cow's milk obtained by repeated operation of ion-exchange chromatography and molecular sieve chromatography ordinarily averages 25–28%.

Ultrafiltration under pH 3.0 by coexistence of citric acid completely removes ferric iron from the molecules, resulting in a fully ferric iron unsaturated form (apo-form). Addition of $Fe^{3+}$ in the presence of calculated amount of $CO_3^-$ converts apo-form to $Fe^{3+}$ saturated forms with desirable saturation levels. The protein containing iron ion by desired degree of saturation, from apo-type or iron free to holo-type or iron-saturated, can be utilized in the invention. Accordingly, the efficacy of the formulated medicine of the invention is unrelated to the degree of iron-saturation.

The protein class of the transferrin/lactoferrin family obtained above can improve host-defense activity which was greatly depressed by Lentiviral infection, and can treat and/or prevent opportunistic infectious disease in mammals (including humans). Concerning the route of administration, oral administration can give sufficient beneficial immunopotentiating effects in hosts. In such special cases as opportunistic infectious disease caused in the oral cavity, skin or eyes, the formulated medicine of the invention can be locally applied as ointments, creams, lotions and eye-drops. Concerning the administration interval, once a day (e.g., in early morning on an empty stomach or before sleep) affords sufficient beneficial effect.

The proteins class of the transferrin/lactoferrin family have weak antimicrobial activities against certain microbes; as the degree of iron saturation decreases, the activities against microbes increase, especially in the medium in which iron is growth-limiting. However, there is no possibility that those proteins, which are taken orally, would be absorbed from the intestine and still have their intact conformations. Therefore, unlike chemotherapies, their antimicrobial activities in vitro cannot contribute to the beneficial effect in vivo in opportunistic infectious diseases. One of the features of the host-mediated effect of the transferrin/lactoferrin family is that the dose-response shows a sigmoid curve and the response reaches the plateau (but not bell-shaped) when the dose exceeds a certain amount. The protein class of transferrin/lactoferrin family shows a sigmoidal dose-response curve, and the minimum effective dose through the oral route ranges from 0.5 to 50 mg/kg.

It is not clarified yet what type of host-related response is caused by oral administration of the protein class of transferrin/lactoferrin family. However the final stage of processing of infected pathogens is definitely accelerated in the host, since in the case of small animals (such as mice and rats) the oral administration of the protein causes enhancement of the phagocytic capacity of phagocytes existing in peripheral blood, pulmonary alveoli, abdominal cavity, etc.

Some examples show a remarkable efficacy of the protein class of transferrin/lactoferrin family for both treating and/or preventing opportunistic infectious diseases complicated by infection with Lentivirus. For example: successive oral administration of 600 mg/day of bovine lactoferrin reduces the frequency of onset of opportunistic infectious diseases (in the case of patients positive for HIV-1 in serological test) and the recurrence of the diseases often occurs after cessation of treatment; the oral administration of the protein class significantly shortens the duration of *Pneumocystis carinii* pneumonia, which is the most serious and life-threatening complication in AIDS; and the treatment makes the duration of Cytomegalovirus or Herpes simplex virus infections shorter. The efficacy of the protein class is also evident by the fact that, in the patient who had lost his weight due to severe diarrhea, the administration of the protein improves appetite and causes a quick regaining of body weight.

On the other hand, infection by FIV, a species of Lentivirus, causes an immunodeficiency after the latent period followed by opportunistic infectious diseases in the respiratory tract and urogenital organs resulting in death. The other usually observed conspicuous symptom of feline immunodeficiency caused by FIV usually observed is stomatitis and gingivitis in the oral cavity. The most common stomatitis observed in cats is aphthae caused by Herpes simplex virus and *Candida albicans* infection; in the former, high fever is observed for a day or two followed by pain in the oral cavity, driveling, ozostomia and negativism. This disease is a typical opportunistic infectious disease with repeat recurrence due to the defect in host-defense activity. Many cats successfully recovered from stomatitis and gingivitis some days after treatment with 10 to 20 mg/kg of the protein class either by topical application as ointment or oral administration. Since it is difficult to recover from stomatitis and gingivitis related to FIV infection because of serious immunodeficiency, and since many result in asthenia leading to death, the efficacy of the protein class is worth noticing.

In addition, long term administration of the protein class of the transferrin/lactoferrin family by a admixture with foods remarkably improved opportunistic diseases in respiratory organs and urogenital organs of FIV infected cats. This fact suggests that the protein of the invention can prevent the onset of infectious diseases caused by proliferation of opportunistic pathogens through enhancement of host-defense ability.

As described above, the protein class of the transferrin/lactoferrin family shows significant efficacy against opportunistic infectious diseases complicated by infection with Lentivirus, both by oral administration and topical application. In addition, administrations of the protein endowed preventative ability against onsets of opportunistic infections, since the frequency of opportunistic infections is significantly reduced by the treatment.

It is remarkable that side effects were hardly observed when the protein class was administered to animals irrespective of the period of administration. A few exceptions are allergic symptoms such as flushes or skin itching when the protein class was administered to those who have milk- or egg-allergy. This kind of side effect could be avoided by patch tests using bovine or hen's protein mixture as allergens before administering the protein class. In the other case, oral administration of large amounts of apo-type protein (more than 20 g at once) to an adult male occasionally caused diarrhea. The cause of this diarrhea can be explained by a direct inflow of the undigested protein in the lower gastrointestinal tract, and this inflow was accompanied with much water into the tract.

The common way of administration of the formulae of the invention is oral, and topical application is also suitable for treating opportunistic infectious diseases occurring in oral cavities, skin, eyes, throat and bronchi. The medicine of the present invention can be use for both treatment and/or prevention of opportunistic infections complicated by Lentivirus infection.

The following materials can be used for the formulae of the invention: milk, skim milk, whey and whey protein containing the native protein class of the transferrin/lactoferrin family and their powder; blood, plasma an serum of a big mammal, e.g., cow, pig or horse, and their powder; albumen and its isolates. The formulae of the invention can be manufactured using those materials into oral tablet, capsule, powder, granules, syrup, ointment, cream or liquid drug-like lotion by common methods known in the art.

To accomplish the present invention, it is not necessary to use highly purified transferrin/lactoferrin protein family, but the biological raw materials rich in this protein family, such as milk, skimmed milk, whey, whey protein mixture, and their powders, mammalian blood from cows, pigs and horses and powders of whole blood, plasma and serum, and egg white or its powdered forms, can be utilized successfully.

The pharmaceutical compositions of the invention may contain the active compounds together with a solid or liquid pharmaceutically acceptable nontoxic carrier. Such pharmaceutical carriers can be sterile liquids, such as water and oils, including those of petroleum, animal, vegetable or synthetic origin, such as peanut oil, soybean oil, mineral oil, sesame oil and the like. Water is a preferential carrier when the pharmaceutical composition is administered intravenously.

Saline solution and aqueous dextrose and glycerol solutions can also be employed as liquid carriers, particularly for injectable solutions. Suitable pharmaceutical excipients include starch, dextrins, glucose, lactose, sucrose, maltose, sorbitol, xylitol, maltitol, gelatin, malt, rice, flour, chalk, silica gel, magnesium carbonate, magnesium stearate, sodium stearate, glycerol monostearate, talc, sodium chloride, dried skim milk, glycerol, propylene glycol, water, ethanol and the like. These compositions can take the form of solutions, suspensions, tablets, pills, capsules, powders, sustained-release formulations and the like. Suitable pharmaceutical carriers are described in "Remington's Pharmaceutical Science" by E. W. Martin. Such compositions will contain an effective therapeutic amount of the active compound together with a suitable amount of carrier so as to provide the form for proper administration to the host. While intravenous injection is very effective form of administration, other modes can be employed.

The protein class of the transferrin/lactoferrin family can be utilized when mixed with foods, e.g., supplemented milk, yoghurt, skim milk powder, lactic acid bacteria fermented milk, chocolates, tablet sweets, and powdered beverages. The most important factor is to avoid protein denaturation during processing by not exceeding a temperature of about 60° C.

EXAMPLE 1

A male adult, 32 years and 8 months old, whose serum was positive for human immunodeficiency virus type-1 (HIV-1), was suddenly attacked by fever, dyspnea, cough and cyanosis. These symptoms suggested the pneumonia caused by *Pneumocystis carinii* and laboratory tests were carried out using the patient's sputum. As expected, *Pneumocystis carinii* was detected in the specimen and the combined treatment with trimethoprim and sulfamethoxazol was initiated immediately. However, the treatment had not improved the symptoms even after 4 days and bovine lactoferrin (purity ca. 90% with 26% ferric iron saturation) at a daily dose of 700 mg was orally given to the patient simultaneously with the chemotherapies mentioned above. Consequently, the body temperature began to decrease after 48 h, and cough and cyanosis were also much improved. Together with these improvements, appetite increased gradually. The body temperature returned to normal 7 days after the lactoferrin treatment, and the patient regained 3.5 kg body weight during the treatment of 4 weeks. Adverse effects, both subjective and objective, were not seen throughout the experimental period in the patient.

EXAMPLE 2

Three HIV-1 positive males (35–42 years old) with recurrent stomatitis and gingivitis were treated with bovine apolactoferrin (purity 87%). Those patients had either aphthae or ulcers on the mucosa of the oral cavity and lip, gingiva, soft palate and tongue, and severely lost appetite due to pain and observed coating of tongue, driveling and stench from the mouth. Before lactoferrin treatment, the patients were treated with topical application of silver nitrite solution, glucocorticoid ointment and injections with multivitamin mixture. However, these treatments gave no beneficial effect on these symptoms and recovery took a long time. Granules containing human apolactoferrin (350 mg/day as lactoferrin, ferric iron saturation is less than 5%) were given to the patients once daily for 4 weeks and the effect was observed. The inflammation in the oral cavity was much ameliorated 6 days later, along with decreased stench from the mouth. Also, the treatment much increased appetite as ameliorating the pain. The ulcers and aphthae disappeared from the oral cavity 8–14 days after the treatment and averaged body weight gain was 3.1 kg (2.4, 3.6 and 3.4 kg each) during 4 weeks. Histopathological examination and culture of the specimens from the oral cavity indicated infection with Herpes simplex virus type-1 and *Candida albicans*. The amelioration suggests that lactoferrin therapy greatly improves the host defense mechanism, successfully removing these pathogens through the immune system. Therefore, it is apparent that oral treatment with lactoferrin shows beneficial effects on stomatitis and gingivitis due to immunodeficiency in HIV-1 infected human beings. Side effects were not observed during the treatment.

EXAMPLE 3

Pneumonia caused by infection with *Pneumocystis carinii* is the leading cause of death among HIV-1 infected patients. Once the pneumonia onsets, the rate of death reaches up to 30%. Three patients (23, 35 and 46 years old, each) recovered from *Pneumocystis carinii* pneumonia participated in this study. They were treated for 6 months with granules containing ovo-transferrin (700 mg daily) extracted from hen's egg-white. The ingestion of the granules was once daily at early in the morning. The recurrence of the pneumonia and opportunistic infections with cytomegalo-virus, herpes simplex virus and *Candida albicans* were monitored during this period. The results indicate that the treatment with ovo-transferrin is highly beneficial for all the patients, since neither the recurrence of *Pneumocystis carinii* pneumonia nor opportunistic infections occurred during this period, and the quality of life of the patients was greatly improved by the treatment. The patients regained body weight of 6.5, 4.0 and 10.8 kg respectively, since they were free from these infections during the experimental period. No side effects were observed throughout the study.

EXAMPLE 4

The most frequent opportunistic infections encountered in feline immunodeficiency virus (FIV) infected cats are stomatitis, gingivitis and chronic infection of the upper air way (upper respiratory tract). FIV-positive cats taken to domestic animal hospitals were orally treated with lactoferrin (20 mg/kg, daily). The lactoferrin used was bovine native lactoferrin with 85% purity and 25% ferric iron saturation. After it was dissolved in distilled water, the solution was sprayed over ulcers and aphthae in the oral cavity of cats with stomatitis and gingivitis caused by FIV and dental calculus. The treatment periods were from 7 days to several months, and the amounts of saliva and stench from the mouth were observed.

Among a total of 11 cases, 4 cases were remarkably improved by lactoferrin treatment and 3 cases were partially improved during the treatment period. It was unclear whether or not the treatment afforded the beneficial effects in the remaining 4 cases. The two cases out of 4 where lactoferrin treatment greatly improved the stomatitis and gingivitis were FIV-positive, where very severe gingivitis and stomatitis were observed and the animals lost appetite due to the pain before the treatment. However, the appetite much increased 7–10 days after the lactoferrin treatment as the pain ameliorated, and resulted in disappearance of the stench from the mouth. Much driveling was again observed after cessation of lactoferrin treatment.

EXAMPLE 5

A total of 9 adult cats positive with FIV (complicated with upper bronchial infection) were randomly allocated into 2 groups as they were taken to domestic animal hospitals. The first group was treated with ovo-transferrin and the others with controls. The experimental period was 8 weeks, and the daily dose of ovo-transferrin was 20 mg/kg that was given to the animals as an admixture of canned fish or animal meats. The controls died due to pneumonia 8, 11, and 34 days after the beginning of the study and only one survived throughout the experimental period, while all animals survived 8 weeks after the study in the ovo-transferrin group. Therefore it is evident that ovo-transferrin is both preventative and curative against chronic upper bronchial infections in FIV-positive cats.

The present invention thus relates to a pharmaceutical composition for treatment and/or prevention of opportunistic infectious diseases complicated by infection with Lentivirus in mammals and for enhancing the efficacy of the host immune system in a mammal in need thereof, containing raw but not denatured proteins belonging to the class of mammalian transferrin/lactoferrin family and optionally a pharmaceutically acceptable carrier.

The present invention also concerns a food product which contains food and an amount of a pharmaceutical composition effective to prevent and/or treat opportunistic infections caused by opportunistic microorganisms, the pharmaceutical composition containing raw but not denatured proteins belonging to the class of mammalian transferrin/lactoferrin family and optionally a pharmaceutically acceptable carrier.

Additionally, the present invention relates to a cream or ointment containing the composition described above or to a tablet containing the composition described above (tabletted either alone or with a pharmaceutically acceptable carrier).

The present invention also relates to several methods:

A method for the prevention and/or treatment of opportunistic disease, involving administering to a mammal in need thereof an amount of the pharmaceutical composition described above, said amount effective to prevent and/or treat said opportunistic disease caused by opportunistic microorganisms.

A method of potentiating the host immune system in a mammal in need thereof, involving optionally adding an amount of raw but not denatured proteins belonging to the class of mammalian transferrin/lactoferrin family, effective to potentiate the host immune system against opportunistic microorganisms, to a pharmaceutically acceptable carrier, and administering the protein and optionally the carrier to the mammal.

A method for the prevention and/or treatment of opportunistic diseases, involving administering to a mammal in need thereof an amount of the food described above, the amount effective to prevent and/or treat opportunistic diseases caused by opportunistic microorganisms.

Further variations and modifications of the foregoing will be apparent to those skilled in the art and such variations and modifications are attended to be encompassed by the claims that are appended hereto.

Japanese Priority Application 93933/92 filed on Mar. 2, 1992 is relied on and incorporated by reference.

U.S. patent application Ser. No. 07/769,766, filed on Oct. 4, 1991, now U.S. Pat. No. 5,198,419 and U.S. patent application Ser. No. 07/624,229, filed on Dec. 7, 1990, are incorporated by reference.

What is claimed:

1. A method of potentiating the host immune system in an immunocompromised mammal in need thereof, comprising adding an amount of raw but not denatured lactoferrin, effective to potentiate the host immune system against opportunistic microorganisms, to a pharmaceutically acceptable carrier, and administering said lactoferrin and carrier to said immunocompromised mammal, wherein the immunocompromised condition is caused by Lentiviral infection, and wherein said opportunistic microorganisms are protozoans or fungi.

2. The method according to claim 1, wherein said protein is present at a dosage of 0.1 to 100 mg/kg/day.

3. The method according to claim 2, wherein said protein is present at a dosage of 0.5 to 50 mg/kg/day.

4. The method according to claim 1, consisting essentially of adding an amount of raw but not denatured lactoferrin, effective to potentiate the host immune system against opportunistic microorganisms, to a pharmaceutically acceptable carrier, and administering said lactoferrin and carrier to said mammal.

5. The method according to claim 1, wherein said opportunistic microorganisms are protozoans.

6. The method according to claim 1, wherein said opportunistic microorganisms are fungi.

7. The method according to claim 1, wherein said administering is oral or topical.

8. The method according to claim 7, wherein said administering is oral.

* * * * *